(12) United States Patent
Christensen et al.

(10) Patent No.: US 8,647,357 B2
(45) Date of Patent: Feb. 11, 2014

(54) LANCET DEVICE WITH FLEXIBLE COVER

(75) Inventors: Curtis Jerome Christensen, Stillwater, MN (US); Daniel William Davis, Hugo, MN (US); Erik Daniel Davis, Hugo, MN (US)

(73) Assignee: Birch Narrows Development LLC, Stillwater, MN (US)

( * ) Notice: Subject to any disclaimer, the term of this patent is extended or adjusted under 35 U.S.C. 154(b) by 181 days.

(21) Appl. No.: 13/234,826

(22) Filed: Sep. 16, 2011

(65) Prior Publication Data

US 2012/0203083 A1 Aug. 9, 2012

Related U.S. Application Data (60) Provisional application No. 61/439,882, filed on Feb. 5, 2011.

(51) Int. Cl.
*A61B 17/32* (2006.01)
(52) U.S. Cl.
USPC ............................................. 606/181; 606/182
(58) Field of Classification Search
None
See application file for complete search history.

(56) References Cited

U.S. PATENT DOCUMENTS

| | | | |
|---|---|---|---|
| 5,054,499 A | | 10/1991 | Swierczek |
| 5,231,993 A | | 8/1993 | Haber et al. |
| 5,402,798 A | * | 4/1995 | Swierczek et al. ............ 600/583 |
| 5,505,212 A | | 4/1996 | Keljmann et al. |
| 5,636,640 A | | 6/1997 | Staehlin |
| 7,959,581 B2 | * | 6/2011 | Calasso et al. ................ 600/583 |
| 2003/0050573 A1 | * | 3/2003 | Kuhr et al. .................... 600/567 |
| 2003/0088191 A1 | * | 5/2003 | Freeman et al. .............. 600/583 |
| 2006/0184189 A1 | * | 8/2006 | Olson et al. ................... 606/181 |
| 2006/0271084 A1 | * | 11/2006 | Schraga ......................... 606/182 |
| 2007/0129620 A1 | | 6/2007 | Krulevitch et al. |
| 2008/0058726 A1 | | 3/2008 | Jina et al. |
| 2009/0099427 A1 | | 4/2009 | Jina et al. |
| 2009/0204027 A1 | * | 8/2009 | Zuk et al. ...................... 600/583 |
| 2010/0023045 A1 | * | 1/2010 | Macho et al. ................. 606/182 |

* cited by examiner

*Primary Examiner* — Shafiqul Haq
*Assistant Examiner* — Gary E Hollinden
(74) *Attorney, Agent, or Firm* — Fredrikson & Byron, P.A.

(57) ABSTRACT

The biological test kit is a device for drawing and, optionally, testing biological samples. The biological test kit is an array of Lancets set in wells in a rigid base. Each lancet well is covered by a protective cover which when deformed permits the lancet to puncture a user or other patient. In one embodiment the biological test kit employs distinct covers for each lancet and in another the covers are formed from sheet material formed into blisters which cover the lancet.

12 Claims, 7 Drawing Sheets

LANCET DEVICE WITH FLEXIBLE COVER

CROSS REFERENCE TO RELATED APPLICATIONS

The application listed below is the only application related to this application. This application claims benefit of the earlier filing date under 35 USC 119(e) of provisional application No. 61/439,882 filed on Feb. 5, 2011.

STATEMENT REGARDING FEDERALLY SPONSORED RESEARCH OR DEVELOPMENT

No invention claimed in this application was made under Federally sponsored research or development.

THE NAMES OF THE PARTIES TO A JOINT RESEARCH AGREEMENT

Not Applicable

REFERENCE TO A SEQUENCE LISTING

Not Applicable

BACKGROUND OF THE INVENTION

1. Field of the Invention

The biological Test Kit relates to the field of patient operated biological testing apparatus 2. Description of Related Art The use of Lancets in biological testing is well known in the art. In some inventions the Lancet is placed in or formed as part of a blister or bubble. A user causes the blister to collapse and thereby move the lancet to puncture the skin of the patient or user. U.S. Pat. No. 5,231,993 to Haber et al, U.S. Pat. No. 5,636,640 to Staehlin, U.S. Pat. No. 5,505,212 to Keljmann et al, U.S. Pat. No. 5,054,499 to Swierczeck, published patent applications 20080058726 to Jina, 20070129620 to Krulevich et al, and 20090099427 also to Jina are all typical of this approach. The present invention provides an array of lancets, each of which is housed and protected in a well which is covered by a flexible cover.

BRIEF SUMMARY OF THE INVENTION

The biological test kit is a device for drawing and, optionally, testing biological samples. The biological test kit comprises: a rigid first layer, one or more lancets secured to the rigid first layer, said lancets each having a sharp region disposed substantially away from the rigid first layer, one or more second layers disposed in an opposed arrangement relative to the rigid first layer, the rigid first layer and second layers being arranged to form one or more cavities, each of the one or more second layers forming one or more covers, each cover over one of the lancets; and each of the one or more covers having a first unconstrained configuration in which the lancet sharp region does not protrude past or through the cover and having a second compressed configuration in which the lancet's sharp region protrudes through the cover. In one embodiment the biological test kit employs distinct covers for each lancet and in another the covers are formed from sheet material formed into blisters which cover the lancet.

DETAILED DESCRIPTION OF THE INVENTION

Figure 1:
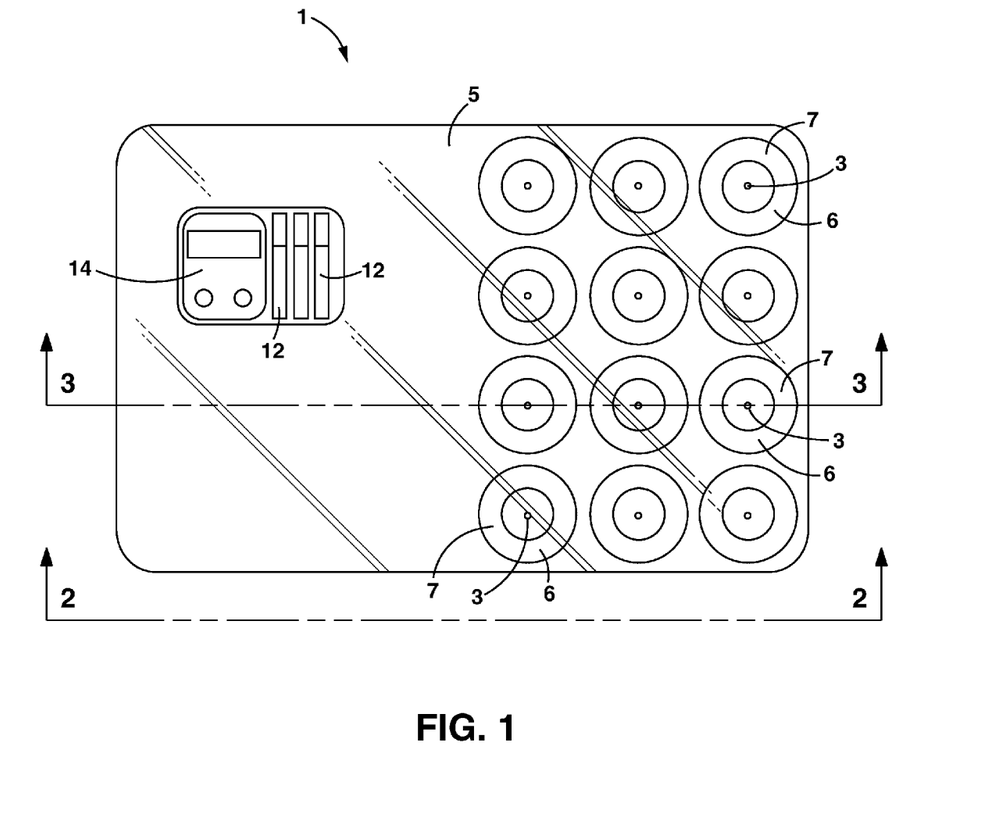
FIG. 1 is a top view of the biological test kit.
Figure 2:
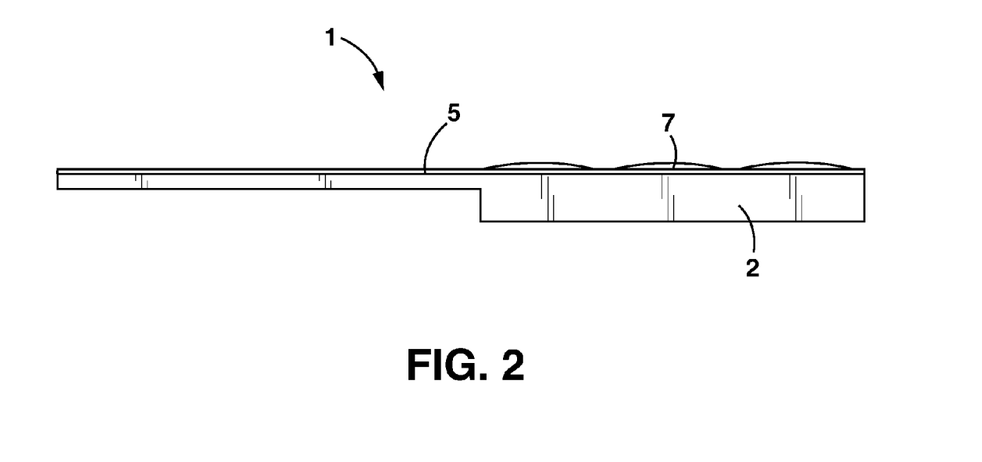
FIG. 2 is a front view taken from FIG. 1.
Figure 3:
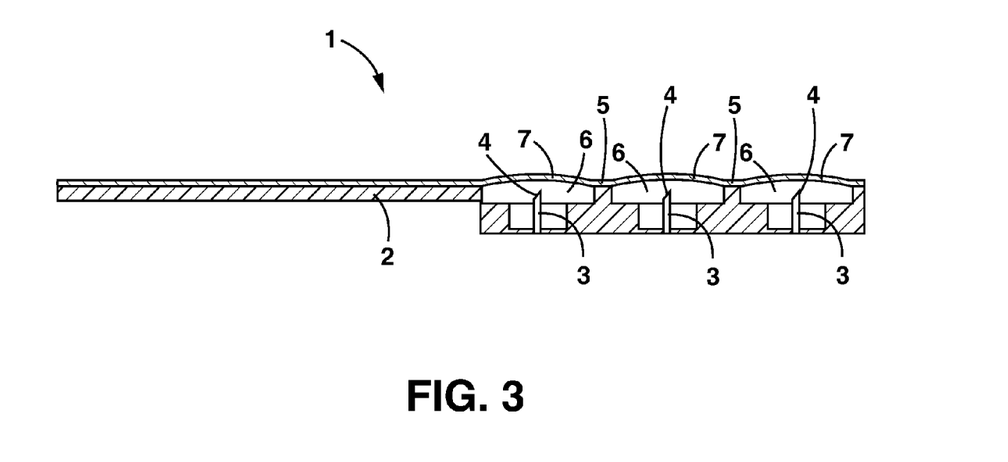
FIG. 3 is a section view taken from FIG. 1.

The biological test kit 1 comprises: a rigid first layer 2, one or more lancets 3 secured to the rigid first layer 2, said lancets 3 each having a sharp region 4 disposed substantially away from the rigid first layer 2, one or more second layers 5 disposed in an opposed arrangement relative to the rigid first layer 2, the rigid first layer 2 and second layers 5 being arranged to form one or more cavities 6 there-between, each of the one or more second layers 5 forming one or more covers 7, each cover 7 over one of the lancets 3; and each of the one or more covers 7 having a first unconstrained configuration 8 in which the lancet 3 sharp region 4 does not protrude past or through the cover 7 and having a second compressed configuration 9 in which the lancet's 3 sharp region 4 protrudes through the cover 7.

The rigid first layer 2 is composed of a rigid material such as plastic, wood, or metal. The rigid first layer 2 provides a foundation for construction of the biological test kit 1.

Lancets 3 are small rods or bars constructed of metal or plastic with one end flattened and sharpened to facilitate making a small puncture site 10, often optimized for puncturing human skin. In the biological test kit 1, one or more lancets 3 are fixed in the rigid first layer 2 such that the sharp region 4 of the lancet 3 is positioned at a distance from the rigid first layer 2. The lancets 3 may be placed in any pattern.

Figure 7:
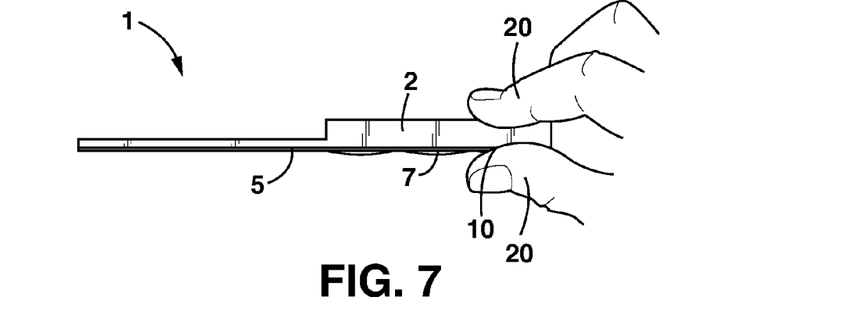
FIG. 7 is a front view of a kit pressed between a thumb and index finger.
Figure 8:
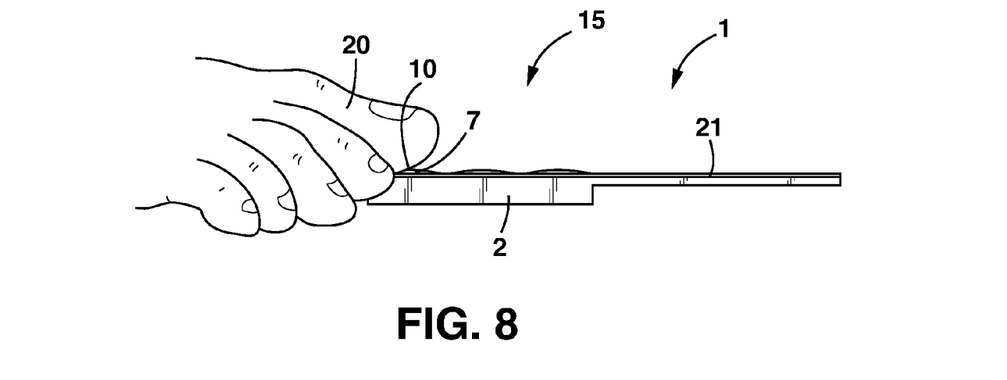
FIG. 8 is a front view of a second embodiment pressed upon a hard surface by another body part.
Figure 9:
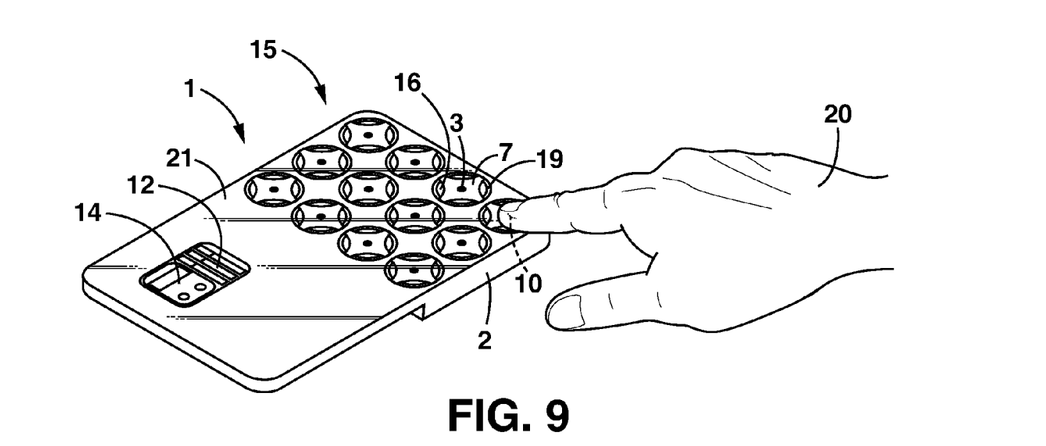
FIG. 9 is a perspective view of a second embodiment in use.

The second layer 5 is made of resilient material and is formed over the rigid first layer 2 to provide a cover 7 for each of the lancets 3. This may be accomplished in any number of ways including, but not limited to, forming the second layer 5 into a number of blisters where each blister forms a cover 7 for one of the lancets 3 and forms an airtight cavity 6 covering and surrounding the lancet 3. These blisters are sized so that when a user applies sufficient compressive force against the rigid first layer 2 and the second layer 5 the blister is pierced by the lancet 3 along with the skin of the user. The user may accomplish this by pinching the blister between a thumb and index finger, or any other suitable body parts 20. Alternatively, the user may apply this pinching force by placing the rigid first layer 2 on a supporting surface and pressing the appropriate body part 20 on the blister. The material chosen for the second layer 5, and therefore the blisters, may be sufficiently resilient to cause the blister to reform into its original position, and cover 7 the lancet 3, when the user applied pressure is removed.

The biological test kit 1 may include any number of second layers 5. However, each of the second layers 5 may serve a unique purpose such as resealing the hole made by passage of the Lancet 3 through the cover 7 or providing a dose of antibiotic, or providing an indication as to the chemical analysis of the biological sample 13.

The biological test kit 1 may also include test strips 12 which capture biological samples 13 resulting from the action of the lancet 3 such as fluid exuded from the puncture site 10 created by the lancet 3.

Figure 14:
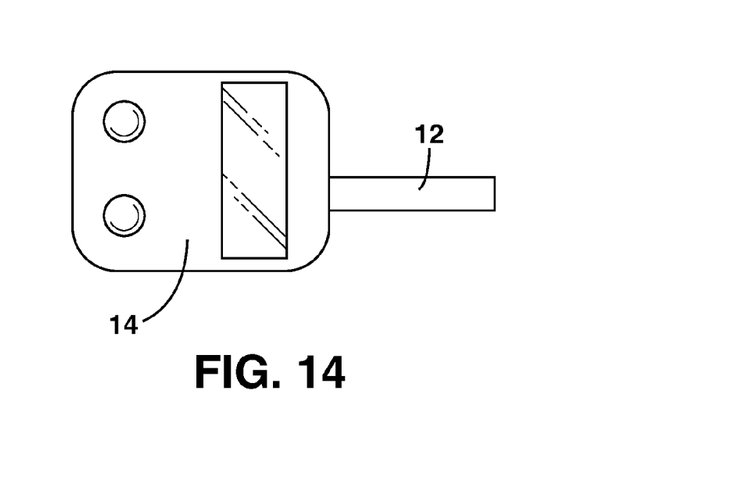
FIG. 14 is a top view of the testing apparatus measuring a sample.

The biological test kit 1 may also include a test apparatus 14 for analysis of the samples 13 gathered as above. This test apparatus 14 may include the ability to display the results of the analysis in any suitable manner, such as a digital readout or color change of the test strip 12.

Figure 4:
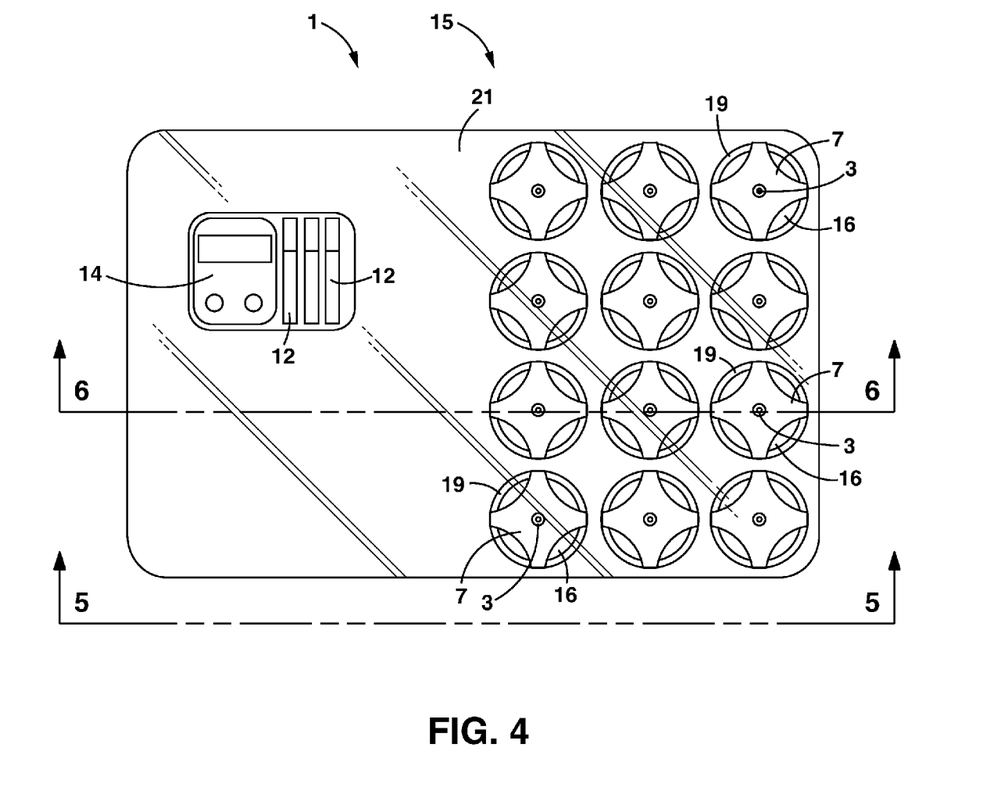
FIG. 4 is a second embodiment of a biological test kit.
Figure 5:
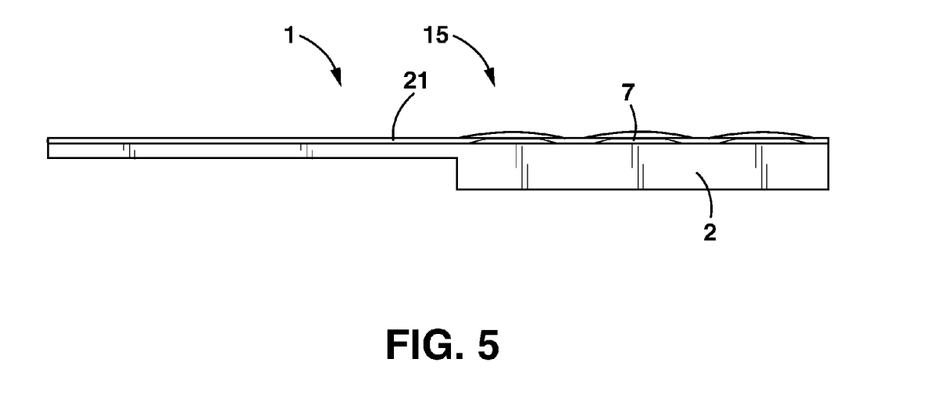
FIG. 5 is a front view taken from FIG. 4.
Figure 6:
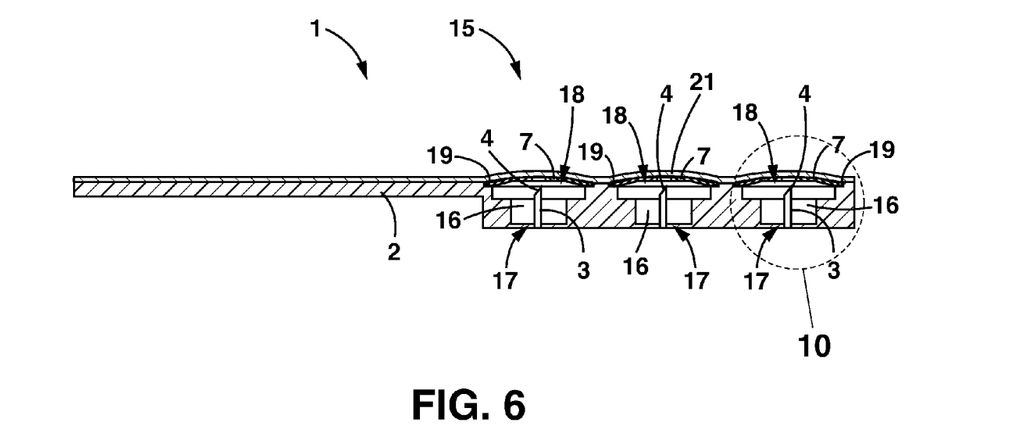
FIG. 6 is a section view taken from FIG. 4.

In a second embodiment 15 the biological test kit 1 includes a rigid first layer 2 and lancets 3 as above with a distinct well 16 provided for each lancet 3 within the rigid first layer 2 and a distinct cover 7 for each lancet 3. Each well 16 has a closed end 17 and an open end 18. A lancet 3 is fixed to the closed end 17 of each well 16. Each well 16 is formed with a ledge 19 around the interior of its open end 18. The well 16 and the ledge 19 are sized to permit insertion of a cover 7 said cover 7 supported by the ledge 19.

Figure 10:
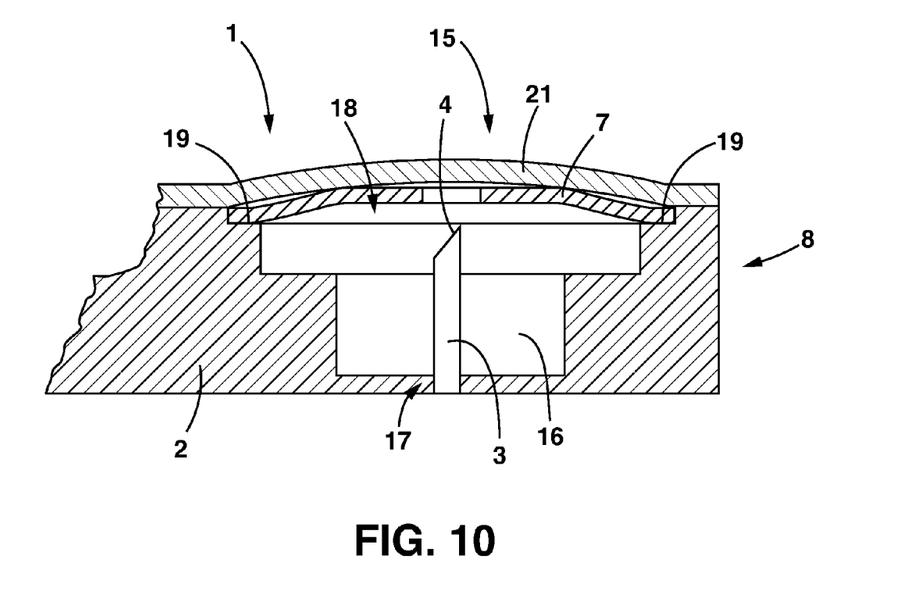
FIG. 10 is an enlarged detail view taken from FIG. 6, in unconstrained configuration.
Figure 11:
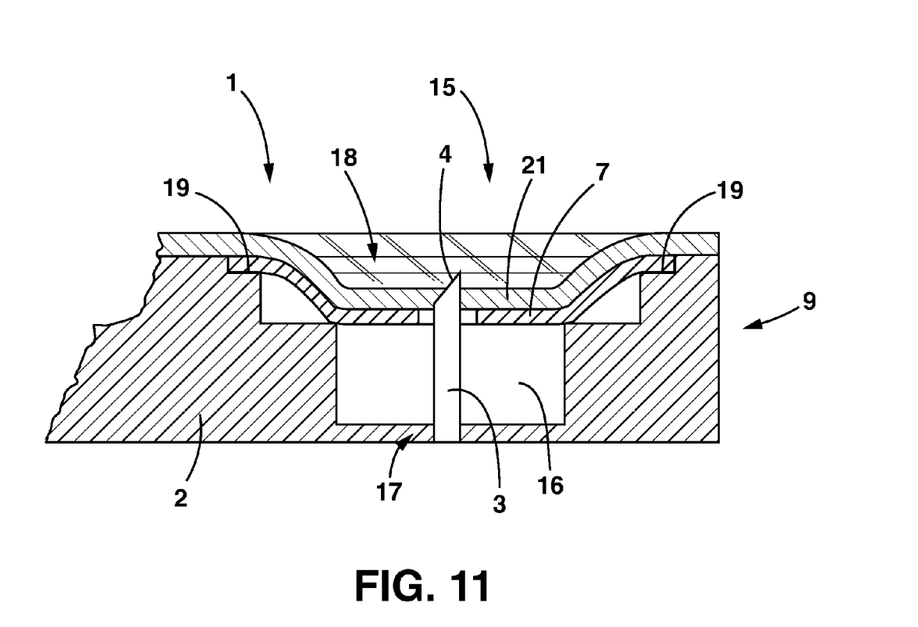
FIG. 11 is a view like FIG. 10 in a compressed configuration.

Each cover 7 is formed as a compound curve and formed from a flexible and resilient material such that the cover 7 can be compressed by an applied force into a compressed configuration 9 and when said force is removed the cover 7 returns to its unconstrained configuration 8. When the cover 7 is placed in the well 16 with the convex surface facing away from the closed end 17 of the well 16 and the cover 7 is in the unconstrained configuration 8 the cover 7 conceals the lancet 3. When so placed and pressed into the compressed configuration 9 the lancet 3 protrudes through the cover 7 to a prescribed distance. When a user desires to produce a puncture site 10 from which a biological sample 13 may be taken, the user presses the cover 7 with sufficient force that the lancet 3 pierces the cover 7 and the user's finger, or other body part 20. It is to be noted that the cover 7 may or may not include a hole through which the lancet 3 passes.

The Biological Test kit 1 may be further provided with one or more protective or indicative layers 21. The protective or indicative layers 21 may be made of a material which is flexible yet non porous to prevent intrusion of foreign material when serving a protective function and made of a chemically reactive material when serving an indicative function or be made of a material suitable for protection and treated with an indicative substance to serve both purposes.

As above the rigid first layer 2 may be provided with a test apparatus 14 and test strips 12.

Figure 12:
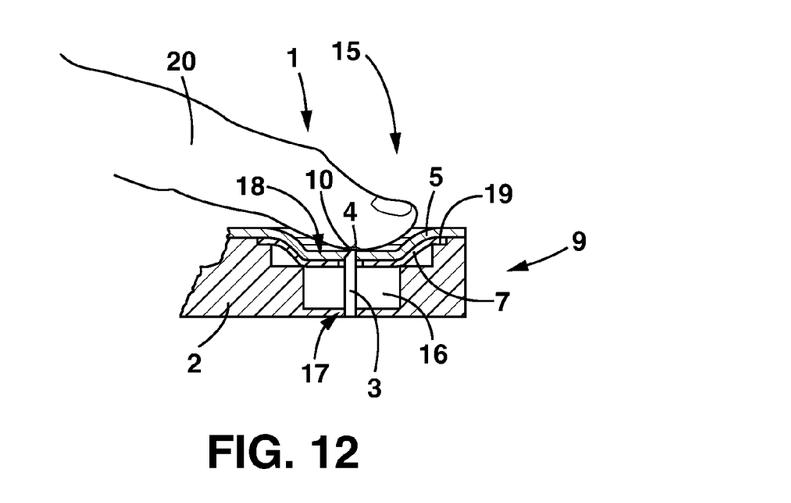
FIG. 12 is a detail view of collecting the biological sample by producing a wound.
Figure 13:
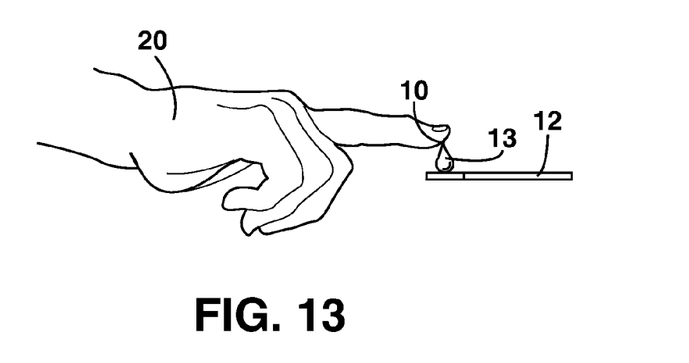
FIG. 13 is a front view of collecting a biological sample from a wound.

The biological test kit 1 may be used according to the following steps: collecting biological samples 13 comprising the steps, compressing a lancet 3 cover 7 onto a stationary lancet 3 until said lancet 3 pierces said cover 7 and said user, producing a puncture site 10. This method may further include the step of collecting biological samples 13 from said puncture site 10. This method may also comprise the step of using a testing apparatus 14 to measure one or more chemical properties of said biological sample 13.

SEQUENCE LISTING

Not Applicable

We claim:
1. A device comprising:
a) a rigid first layer;
b) one or more lancets secured to the first layer, the one or more lancets and the first layer being stationary relative to one another, said lancets each having a sharp region disposed substantially away from the first layer;
c) one or more second layers disposed in an opposed arrangement relative to the first layer, the first and second layers being arranged to form one or more cavities there-between, each of the one or more second layers forming one or more covers, each cover over one of the lancets; and
d) each of the one or more covers having a first unconstrained configuration in which the lancet sharp region does not protrude past or through the cover and having a second compressed configuration in which the lancet sharp region protrudes through the cover.

2. The device of claim 1 wherein said covers are resilient such that the cover can pass from the unconstrained configuration to the compressed configuration when a compression force is applied and return from the compressed configuration to the unconstrained configuration when said compression force is removed.

3. The device of claim 1 further comprising: a) at least one chemical test strip for capturing biological samples.

4. The device of claim 3 further comprising a testing apparatus for testing one or more chemical properties of biological samples present on said test strip.

5. A device comprising:
a) a rigid first layer,
b) one or more lancets secured to the first layer, the one or more lancets and the first layer being stationary relative to one another, said lancets each having a sharp region disposed substantially away from the first layer;
c) one or more covers disposed in an opposed arrangement relative to the first layer, each cover covering at least one of said lancets, and said lancet disposed within a well formed in said first layer, said cover disposed to cover said well; and
d) each of the one or more covers having a first unconstrained configuration in which the lancet sharp region does not protrude past or through the cover and having a second compressed configuration in which the lancet sharp region protrudes through the cover.

6. The device of claim 5 wherein said covers are resilient such that the cover can pass from the unconstrained configuration to the compressed configuration when a compression force is applied and return from the compressed configuration to the unconstrained configuration when said compression force is removed.

7. The device of claim 5 further comprising a protective layer covering the one or more covers.

8. The device of claim 5 further comprising: a) at least one chemical test strip for capturing biological samples.

9. The device of claim 8 further comprising a testing apparatus for testing one or more chemical properties of biological samples present on said test strip.

10. A method of drawing a biological sample comprising:
(a) providing a device that includes:
(i) a rigid first layer,
(ii) a lancet secured to the first layer, said lancet having a sharp region disposed substantially away from the first layer, and
(iii) a second layer disposed in an opposed arrangement relative to the first layer, the first and second layers being arranged to form a cavity therebetween, the second layer forming a cover over the lancet;
(b) pressing the cover toward the first layer with a body part to move the cover from an unconstrained configuration in which the lancet sharp region does not protrude through the cover to a compressed configuration in which the lancet sharp region protrudes through the cover and pierces the body part to produce the biological sample, the first layer and the lancet being stationary relative to one another during pressing.

11. The method of claim 10, further comprising:
(c) collecting the biological sample.

12. The method of claim 11, further comprising:
(d) using a testing apparatus to measure one or more chemical properties of the biological sample.

* * * * *